United States Patent [19]

Wei

[11] Patent Number: 5,648,253

[45] Date of Patent: Jul. 15, 1997

[54] INHIBITOR-RESISTANT UROKINASE

[75] Inventor: Cha-Mer Wei, Worcester, Mass.

[73] Assignee: TSI Corporation, Worcester, Mass.

[21] Appl. No.: 942,157

[22] Filed: Sep. 8, 1992

Related U.S. Application Data

[63] Continuation of Ser. No. 631,673, Dec. 20, 1990, abandoned.

[51] Int. Cl.$^6$ ............................ C12N 9/72; C12N 15/55; C12N 15/79; A61K 38/49
[52] U.S. Cl. ..................... 435/215; 424/94.64; 435/69.8; 435/172.3; 800/2
[58] Field of Search ...................... 435/2.5, 69.8, 435/172.3; 424/94.64; 930/240; 800/2

[56] References Cited

U.S. PATENT DOCUMENTS 5,112,755  5/1992  Heyneker et al. ........................ 435/215

OTHER PUBLICATIONS

Madison et al. Nature 339 pp. 721–723 (1989).
Strassberger et al. Febs vol. 157 pp. 219–223 (1983).
Collen, et al., *Drugs* 38: 346–388 (1989).
Haber, et al., *Science*, 243: 51–56 (1989).
Higgins and Bennett, *Ann. Rev. Pharmacol. Toxicol.* 30: 91–121 (1990).
Mayer, *Clin. Biochem.* 23: 197–211 (1990).
Runge, et al., *Circulation* 79: 217–224 (1989).
Appella, et al., *J. Biol. Chem.* 262:4437–4440 (1987).
Loskutoff and Edigington, *J. Biol. Chem.* 256: 4142–4145 (1981).
Kawano, et al., *Nature* 217: 253–254 (1968).
Stump, et al., *J. Biol. Chem.* 261: 12759–12766 (1986).
Archbald, et al., *Proc. Natl. Acad. Sci. USA* 87, 5178–5182 (1990).
Clark, et al., *Bio/Technology* 7, 487–492 (1989).
Simons, et al., *Nature* 328, 530–533 (1987).
Gordon, et al., *Biotechnology* 5, 1183–1187 (1987).
Clark, et al., *Trends in Biotechnology*, 5, 20–24 (1987).

*Primary Examiner*—Dian C. Jacobson

[57] ABSTRACT

Mutants of human urokinase are produced which have an altered amino acid sequence in the domain responsible for binding of plasminogen activator inhibitor(s). One example of an inhibitor resistant mutant is described in detail. Six amino acids (179–184), R H R G G S, have been deleted from the mature urokinase. The gene encoding inhibitor resistant preprourokinase is chemically synthesized according to computer-designed nucleotide sequences containing convenient restriction endonuclease cleavage sites, a signal for the initiation of translation, a sequence encoding the signal peptide of mouse whey acid protein and a complete coding sequence for mature inhibitor-resistant urokinase. The gene was used to transform cultured mouse cells to produce clones that stably incorporate the gene in the genome. Clones with high levels of expression were used as the hosts for production of this protein. Alternatively, the DNA for the inhibitor-resistant prourokinase/urokinase, in combination with a tissue specific promoter, could be introduced into fertilized embryos, the embryo implanted into a suitably prepared female of the same species, and the offspring analyzed for presence of the prourokinase/urokinase gene. The transgenic animals can then be bred and the urokinase produced in the milk.

7 Claims, 6 Drawing Sheets

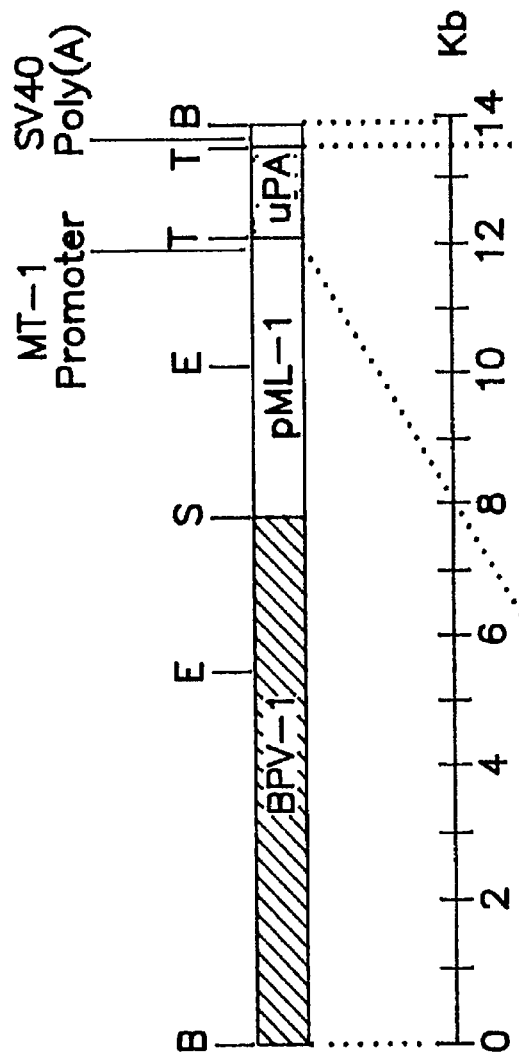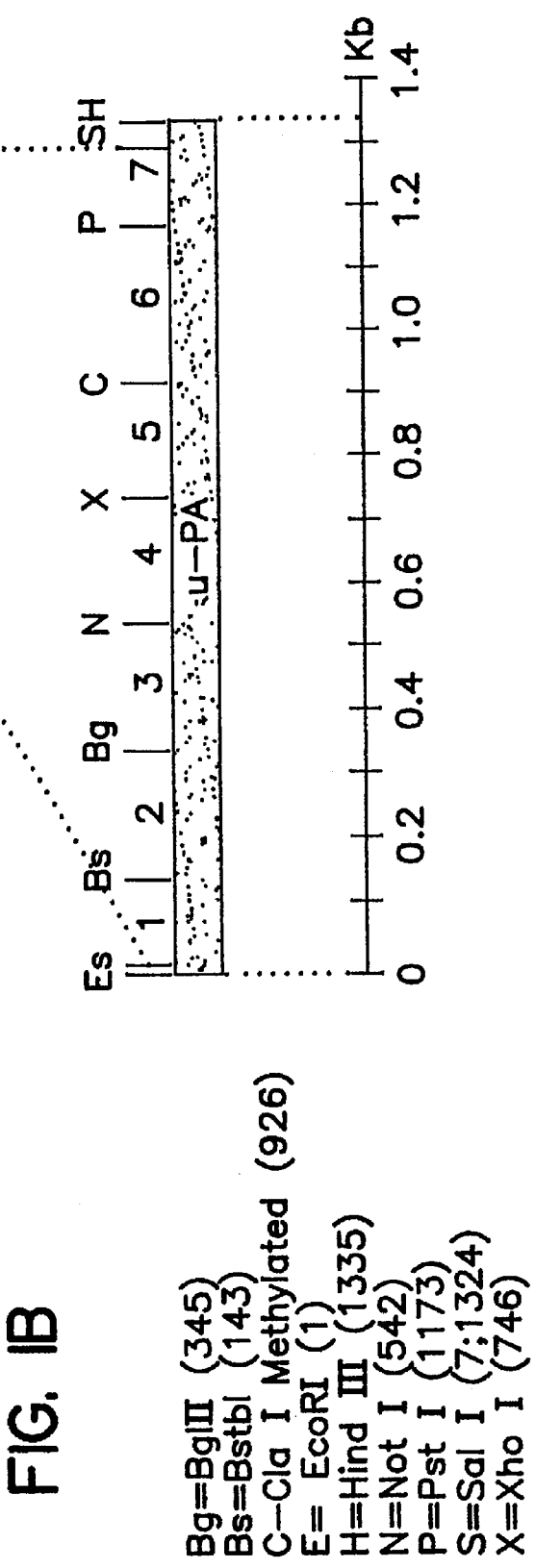
FIG. 1A
B=BamHI (1;138-46)
E=EcoRI (5608; 10286)
S=SalI (7945)
T=TaqI (old SalI-XhoI)
 (12286; 13603)
FIG. 1B
Bg=BglII (345)
Bs=Bstbl (143)
C=Cla I Methylated (926)
E= EcoRI (1)
H=Hind III (1335)
N=Not I (542)
P=Pst I (1173)
S=Sal I (7;1324)
X=Xho I (746)

FIG. 2

```
         M  R  C  L  I  S  L  V  L  G  L  L  A  L  E  V  A  L  A  S  N  E  L  H  Q  V  P  S  N  C  D  C
GAATTCGTCGACGGATCACCAGTACCATGCGTTGCCTCATCAGCCTGGTTCTTGGCCTGCTGGCCCTCGAAGTAATGAGCTTCACCAGGTACCTTCAAACTGTGACT

L  N  G  G  T  C  V  S  N  K  Y  F  S  N  I  H  W  C  N  C  P  K  K  F  G  G  Q  H  C  E  I  D  K  S  K  T  C  Y  E  G
GTCTGAACGGAGGAACCTGTGTTTCGAACAAGTATTTCTCCAACATTCACTGGTGCAACTGCCCAAAGAAATTTGGTGGCCAGCACTGTGAGATAAGTCAAAGACATGCTATGAGG

N  G  H  F  Y  R  G  K  A  S  T  D  T  M  G  R  P  C  L  P  W  N  S  A  T  V  L  Q  Q  T  Y  H  A  H  R  S  D  A  L  Q
AATGGTCACTTCTACCGAGGAAAGGCGAGCACAGACACAATGGGTCGGCCGTGCCTGCCGTGGAACTCTGCCACAGTCCTTCAGCAGACCTACCATGCCCACAGATCTGATGCTCTGC

L  G  L  G  K  H  N  Y  C  R  N  P  D  N  R  R  R  P  W  C  Y  V  Q  V  G  L  K  P  L  V  Q  E  C  M  V  H  D  C  A  D
AACTAGGCCTGGGCAAACACATTACTGCCGAACCCTGACAACCGGCGGCGGCCGACCCTGGTCTGTGCAGGTGGGCTAAAGCCCTGGTCCAAGAATGCATGGTCATGACTGTGCTG

G  K  K  P  S  S  P  P  E  E  L  K  F  Q  C  G  Q  K  T  L  R  P  R  F  K  I  I  G  G  E  F  T  T  I  E  N  Q  P  W  F
GGAAAGAAGCCCTCCTCGCCTCCGGAGGAGCTGAAGTTCCAGTGTGGTCAGAAGACCCTGCGCCCGCGCTTTAAGATTATTGGAGGAGAGTTCACTACCATTGAGAATCAGCCATGGT

A  A  I  Y  R  H  R  G  G  S  V  T  Y  V  C  G  G  S  L  M  S  P  C  W  V  I  S  A  T  H  C  F  I  D  Y  P  K  K  E
TCGCAGCCATCTACCGACATCGAGGACCGAGGAGGATCGGTGACCTATGTGTGTGGTGGAAGCCTCATGAGTCCTTGCTGGGTGATATCTGCCACCCACTGCTTCATTGACTACCCAAAGAAGG

D  Y  I  V  Y  L  G  R  S  R  L  N  S  N  T  Q  G  E  H  K  F  E  V  E  N  L  I  L  M  K  D  Y  S  A  D  T  L  A  H  H
GACTACATTGTCTACCTGGGTCGCTCGAGGCTGAACTCCAACACCCAGGGAGAGATGAAGTTTGAGGTGGAGAACCTCATCTTGCACAAGGACTACTCCGGGGACACCCTGGCCACC

N  D  I  A  L  L  K  I  R  S  K  E  G  R  C  A  Q  P  S  R  T  I  Q  T  I  C  L  P  S  M  Y  N  D  P  Q  F  G  T  S  C
ATAATGATATTGCCTTGCTGAAGATACGTAGCAAGGAGGGCCGGTGTGCACAGCCATCCAGAGACTATCCAGAGAGCAGCTGAAAATGACAGTCGTAAAGCTGATCGATGTACAATGATCCTCAGTTTGGCACCTCCT

E  I  T  G  F  G  K  E  N  S  T  D  Y  L  Y  P  E  Q  L  K  M  T  V  V  K  L  I  S  H  R  E  C  Q  Q  P  H  Y  Y  G  S
GTGAGATCACTGGCTTTGGAAAAGAGAATAGCACAGATTACCTCTATCCAGAGCAGCTGAAAATGACAGTGGTAAAGCTGATCAGTCACCGGGAGTGTCAGCAGCCCCACTACTATGGCT

V  S  W  G  R  G  C  A  L  K  D  K  P  G  V  Y  T  R  V  S  H  F  L  P  W  I  R  S  H  T  K  E  E  N  G  L  A  L  *
CTGAAGTGACAACACCAAAATGTGTGTGCGGACCCGGCCGATTCTGCGGACCGCGGTACAGCTCCTGCAGGGCCGATGCTGACTGCTGACAGGAAGCTCTGAAGCTTAGCAAGCTCTGAAAGCAA

TTGTTTCCTGGGGCCGAGGATGTGCACTGAAAAGACAAGCCCGGTGTCACACACGCGGTGTCACACCTTCCTGCCCTGGAAATACCGGTGTCACACTTCCTGCCCTGGATACCGGTGTCACACTTCCTGCCCTGGAA
TTCGTCGACAAGCTT    1335
```

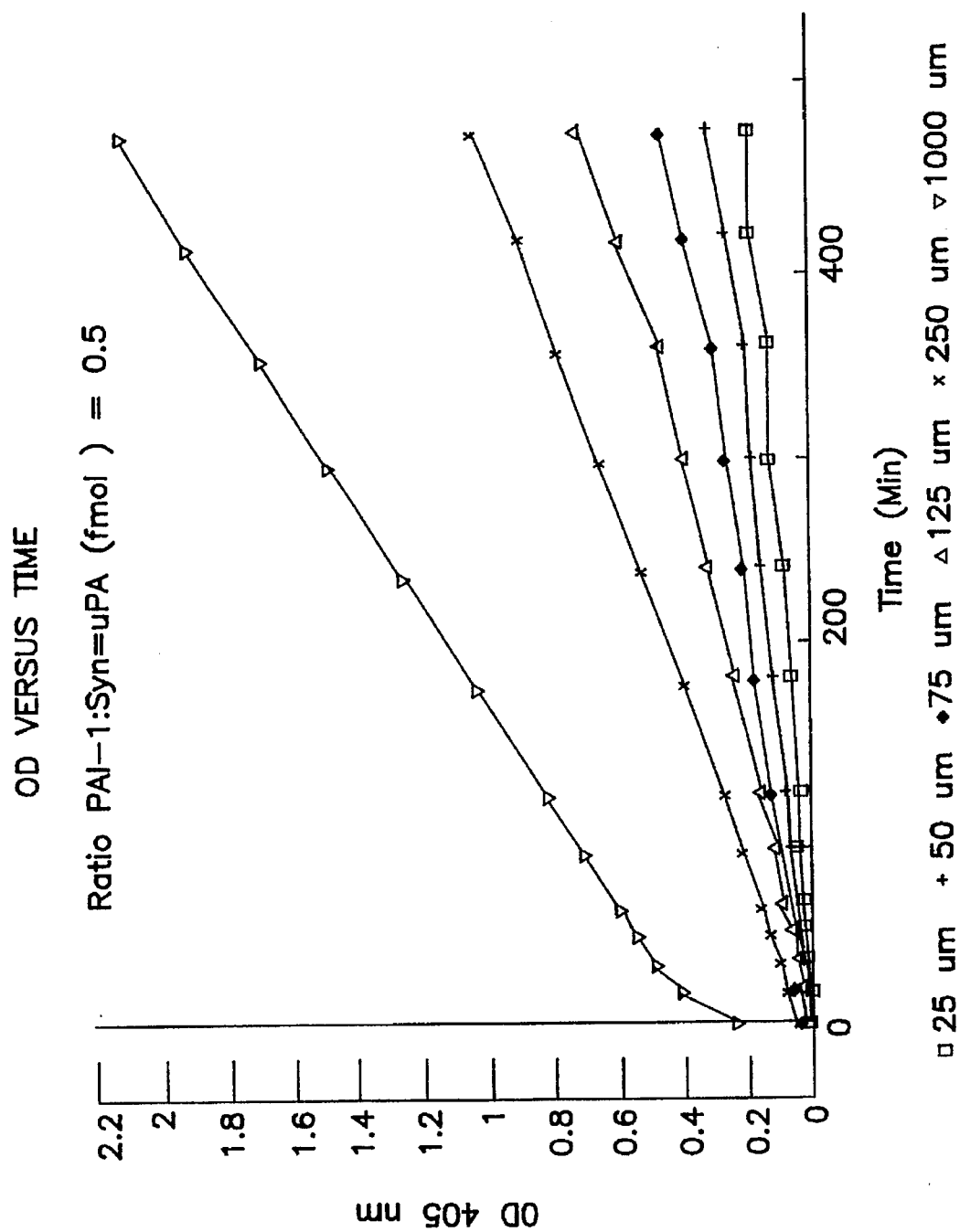

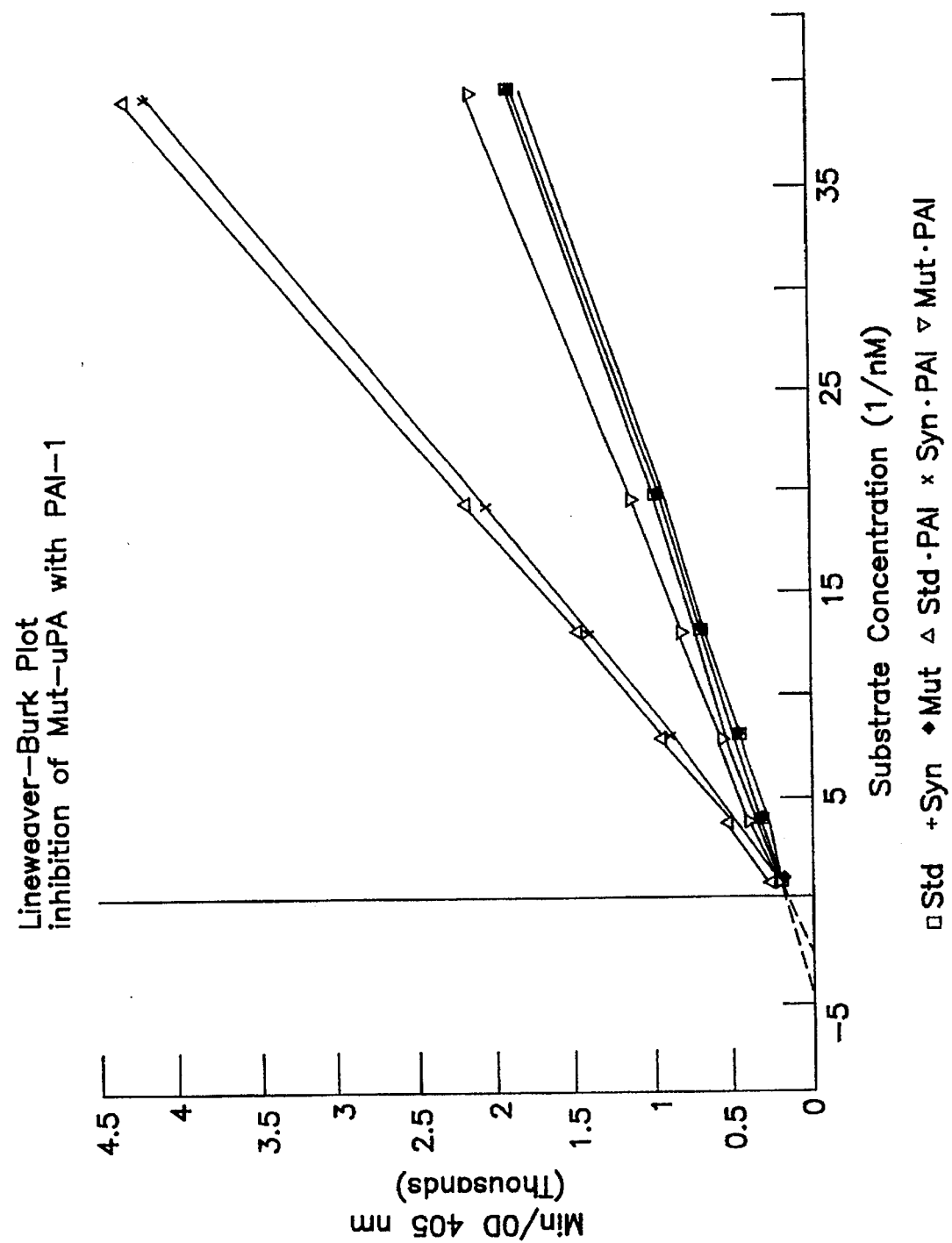

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens ( x i ) SEQUENCE DESCRIPTION: SEQ ID NO:1:

```
Arg  His  Arg  Gly  Gly  Ser
 1                    5
```

( 2 ) INFORMATION FOR SEQ ID NO:2:

( i ) SEQUENCE CHARACTERISTICS:
        ( A ) LENGTH: 1335 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: misc_signal
        ( B ) LOCATION: 27..83
        ( C ) IDENTIFICATION METHOD: experimental
        ( D ) OTHER INFORMATION: /function="WAP signal peptide"
            / evidence=EXPERIMENTAL ( i x ) FEATURE:
        ( A ) NAME/KEY: mutation
        ( B ) LOCATION: replace(618..635, "")

( x i ) SEQUENCE DESCRIPTION: SEQ ID NO:2:

```
GAATTCGTCG ACGGATCACC AGTACCATGC GTTGCCTCAT CAGCCTTGTT CTTGGCCTGC      60
TGGCCCTGGA GGTGGCCCTC GCGAGTAATG AGCTTCACCA GGTACCTTCA AACTGTGACT     120
GTCTGAACGG AGGAACCTGT GTTTCGAACA AGTATTTCTC CAACATTCAC TGGTGCAACT     180
GCCCAAAGAA ATTTGGTGGC CAGCACTGTG AGATAGATAA GTCAAAGACA TGCTATGAGG     240
GAAATGGTCA CTTCTACCGA GGAAAGGCGA GCACAGACAC AATGGGTCGG CCGTGCCTGC     300
CCTGGAACTC TGCCACAGTC CTTCAGCAGA CCTACCATGC CCACAGATCT GATGCTCTGC     360
AACTAGGCCT GGGCAAACAC AATTACTGCC GGAACCCTGA CAACCGGCGG CGACCCTGGT     420
GCTATGTGCA GGTGGGCCTA AAGCCCCTGG TCCAAGAATG CATGGTGCAT GACTGTGCTG     480
```

-continued

```
ATGGCAAGAA GCCCTCCTCG CCTCCGGAGG AGCTGAAGTT CCAGTGTGGT CAGAAGACCC      540
TGCGGCCGCG CTTTAAGATT ATTGGAGGAG AGTTCACTAC CATTGAGAAC CAGCCATGGT      600
TCGCAGCCAT CTACCGGAGG CACCGAGGAG GATCGGTGAC CTATGTGTGT GGTGGGAGCC      660
TCATGAGTCC TTGCTGGGTG ATATCTGCCA CCCACTGCTT CATTGACTAC CCAAAGAAGG      720
AAGACTACAT TGTCTACCTG GGTCGCTCGA GGCTGAACTC CAACACCCAG GGAGAGATGA      780
AGTTTGAGGT GGAGAACCTC ATCTTGCACA AGGACTACTC CGCGGACACC CTGGCCCACC      840
ATAATGATAT TGCCTTGCTG AAGATACGTA GCAAGGAGGG CCGGTGTGCA CAGCCATCCA      900
GGACCATACA GACCATCTGC CTGCCATCGA TGTACAATGA TCCTCAGTTT GGCACCTCCT      960
GTGAGATCAC TGGCTTTGGA AAAGAGAACA GTACTGACTA CCTCTATCCA GAGCAGCTGA     1020
AAATGACAGT CGTAAAGCTG ATCAGTCACC GGGAGTGTCA GCAGCCCCAC TACTATGGCT     1080
CTGAAGTGAC AACCAAAATG CTGTGTGCTG CGGACCCACA GTGGAAAACA GATTCCTGCC     1140
AGGGCGATTC TGGCGGACCG CTTGTATGTT CCCTGCAGGG CCGCATGACT CTGACAGGAA     1200
TTGTTTCCTG GGGCCGAGGA TGTGCACTGA AGACAAGCC CGGTGTCTAC ACACGCGTGT      1260
CACACTTCCT GCCCTGGATA CGGTCCCACA CCAAGGAAGA GAATGGTCTG GCCCTCTGAA     1320
TTCGTCGACA AGCTT                                                      1335
```

( 2 ) INFORMATION FOR SEQ ID NO:3:

( i ) SEQUENCE CHARACTERISTICS:
        ( A ) LENGTH: 430 amino acids
        ( B ) TYPE: amino acid
        ( D ) TOPOLOGY: linear ( i i ) MOLECULE TYPE: protein ( i i i ) HYPOTHETICAL: NO ( i x ) FEATURE:
        ( A ) NAME/KEY: Peptide
        ( B ) LOCATION: 1..19
        ( D ) OTHER INFORMATION: /label=peptide
            / note="WAP signal"

( i x ) FEATURE:
        ( A ) NAME/KEY: Modified-site
        ( B ) LOCATION: 198..203
        ( D ) OTHER INFORMATION: /label=modified
            / note="six amino acids deleted in mutant"

( x i ) SEQUENCE DESCRIPTION: SEQ ID NO:3:

```
Met Arg Cys Leu Ile Ser Leu Val Leu Gly Leu Leu Ala Leu Glu Val
 1               5                  10                  15

Ala Leu Ala Ser Asn Glu Leu His Gln Val Pro Ser Asn Cys Asp Cys
                20                  25                  30

Leu Asn Gly Gly Thr Cys Val Ser Asn Lys Tyr Phe Ser Asn Ile His
            35                  40                  45

Trp Cys Asn Cys Pro Lys Lys Phe Gly Gly Gln His Cys Glu Ile Asp
        50                  55                  60

Lys Ser Lys Thr Cys Tyr Glu Gly Asn Gly His Phe Tyr Arg Gly Lys
    65                  70                  75                  80

Ala Ser Thr Asp Thr Met Gly Arg Pro Cys Leu Pro Trp Asn Ser Ala
                    85                  90                  95

Thr Val Leu Gln Gln Thr Tyr His Ala His Arg Ser Asp Ala Leu Gln
                100                 105                 110

Leu Gly Leu Gly Lys His Asn Tyr Cys Arg Asn Pro Asp Asn Arg Arg
            115                 120                 125
```

| | | | | | | | | | | | | | | |
|---|---|---|---|---|---|---|---|---|---|---|---|---|---|---|
| Arg | Pro 130 | Trp | Cys | Tyr | Val | Gln 135 | Val | Gly | Leu | Lys | Pro 140 | Leu | Val | Gln | Glu |
| Cys 145 | Met | Val | His | Asp | Cys 150 | Ala | Asp | Gly | Lys | Lys 155 | Pro | Ser | Ser | Pro | Pro 160 |
| Glu | Glu | Leu | Lys | Phe 165 | Gln | Cys | Gly | Gln | Lys 170 | Thr | Leu | Arg | Pro | Arg 175 | Phe |
| Lys | Ile | Ile | Gly 180 | Gly | Glu | Phe | Thr | Thr 185 | Ile | Glu | Asn | Gln | Pro 190 | Trp | Phe |
| Ala | Ala | Ile 195 | Tyr | Arg | Arg | His | Arg 200 | Gly | Gly | Ser | Val | Thr 205 | Tyr | Val | Cys |
| Gly | Gly 210 | Ser | Leu | Met | Ser | Pro 215 | Cys | Trp | Val | Ile | Ser 220 | Ala | Thr | His | Cys |
| Phe 225 | Ile | Asp | Tyr | Pro | Lys 230 | Lys | Glu | Asp | Tyr | Ile 235 | Val | Tyr | Leu | Gly | Arg 240 |
| Ser | Arg | Leu | Asn | Ser 245 | Asn | Thr | Gln | Gly | Glu 250 | Met | Lys | Phe | Glu | Val 255 | Glu |
| Asn | Leu | Ile | Leu 260 | His | Lys | Asp | Tyr | Ser 265 | Ala | Asp | Thr | Leu | Ala 270 | His | His |
| Asn | Asp | Ile 275 | Ala | Leu | Leu | Lys | Ile 280 | Arg | Ser | Lys | Glu | Gly 285 | Arg | Cys | Ala |
| Gln | Pro 290 | Ser | Arg | Thr | Ile | Gln 295 | Thr | Ile | Cys | Leu | Pro 300 | Ser | Met | Tyr | Asn |
| Asp 305 | Pro | Gln | Phe | Gly | Thr 310 | Ser | Cys | Glu | Ile | Thr 315 | Gly | Phe | Gly | Lys | Glu 320 |
| Asn | Ser | Thr | Asp | Tyr 325 | Leu | Tyr | Pro | Glu | Gln 330 | Leu | Lys | Met | Thr | Val 335 | Val |
| Lys | Leu | Ile | Ser 340 | His | Arg | Glu | Cys | Gln 345 | Gln | Pro | His | Tyr | Tyr 350 | Gly | Ser |
| Glu | Val | Thr 355 | Thr | Lys | Met | Leu | Cys 360 | Ala | Ala | Asp | Pro | Gln 365 | Trp | Lys | Thr |
| Asp | Ser 370 | Cys | Gln | Gly | Asp | Ser 375 | Gly | Gly | Pro | Leu | Val 380 | Cys | Ser | Leu | Gln |
| Gly 385 | Arg | Met | Thr | Leu | Thr 390 | Gly | Ile | Val | Ser | Trp 395 | Gly | Arg | Gly | Cys | Ala 400 |
| Leu | Lys | Asp | Lys | Pro 405 | Gly | Val | Tyr | Thr | Arg 410 | Val | Ser | His | Phe | Leu 415 | Pro |
| Trp | Ile | Arg | Ser 420 | His | Thr | Lys | Glu | Glu 425 | Asn | Gly | Leu | Ala | Leu 430 | | |

INHIBITOR-RESISTANT UROKINASE

This is a continuation of U.S. Ser. No. 07/631,673 filed Dec. 20, 1990, now abandoned.

BACKGROUND OF THE INVENTION

This invention is generally in the area of genetically engineered urokinases, and in particular relates to an urokinase that is more resistant to inhibition by plasminogen activator inhibitors, and which can be selectively expressed and secreted from the mammary glands of a transgenic animal.

Plasminogen activators (PAs) catalyze the conversion, by limited proteolysis, of the circulating zymogen plasminogen to the broad spectrum protease plasmin, as reviewed, for example, by Collen, et al., Drugs 38: 346–388 (1989); Haber, et al., Science 243:51–56 (1989); Higgins and Bennett, Ann. Rev. Pharmacol. Toxicol. 30: 91–121 (1990); Mayer, Clin. Biochem. 23: 197–211 (1990); and Runge, et al., Circulation 79: 217–224 (1989).

Mammalian plasminogen activators are represented by two types of enzymes: tissue-type (t-PA) and urokinase-type (u-PA). Both enzymes can exist in single or two-chain (a- and b-chain) forms. Plasmin cleaves the activator at a single unique site, Lys158-Ile159 for u-PA and Arg275-Ile276 for t-PA. Cleavage does not alter the activator's molecular weight since the a and b-chains are held together by disulfide bonds. The single-chain form of t-PA (sct-PA) is an active enzyme, whereas the similar form of u-PA (scu-PA) is an inactive zymogen.

u-PA consists of an E-domain (Ser1-Asp45), Kringle-1 (Cys50-Cys131), and P-domain (Ile159-Leu411) containing the catalytic triad His204, Asp255, Ser356. The u-PA a-chain consists of the E-domain and Kringle-1. The E-domain of u-PA has been shown to function as a receptor-binding site by Appella, et al., J. Biol. Chem. 262:4437–4440 (1987).

To prevent systemic activation of plasminogen, the regulation of PA activity involves plasminogen activator inhibitors (PAIs). PAI-1 (originally designated endothelial type by Loskutoff and Edgington, J. Biol. Chem. 256: 4142–4145 (1981)), PAI-2 (originally designated placental type by Kawano, et al., Nature 217: 253–254 (1968)), and PAI-3 (originally designated urine type by Stump, et al., J. Biol. Chem. 261: 12759–12766 (1986)) are members of the serpin (serine protease inhibitor) superfamily. The inhibitors appear to function like other serine protease inhibitors, forming inactive covalent complexes with the target protease. PAI-1 rapidly inactivates both t-PA and u-PA. It is the major PAI of plasma, except during pregnancy. PAI-2 reacts more readily with u-PA than t-PA. PAI-2 is undetectable in the plasma of men and nonpregnant women, but rises to very high levels during late pregnancy.

The gene for urokinase has been characterized, and the protein produced, using recombinant techniques, as well as isolated from urine. Expression and secretion in the milk of transgenic animals has also been proposed, as described in U.S. Pat. No. 4,873,316 to Meade, et al.

For some time, u-PA, t-PA, and another structurally unrelated plasminogen activator, streptokinase, have been used as fibrinolytic therapeutic agents. The therapeutic goal is to dissolve heart attack-causing clots before they cause permanent damage to heart muscle, usually within four to six hours of the clot formation.

There are clinical advantages and disadvantages for each type of PA. Currently, streptokinase is the most affordable. However, t-PA theoretically has one major advantage over streptokinase. When t-PA binds fibrin, the Michaelis constant for the activation of plasminogen decreases by 100 fold, down to the in vivo concentration of plasminogen, as described by Hoylaerts, et al., J. Biol. Chem. 257: 2912–2919 (1982). t-PA therefore functions subsequent to binding fibrin in the clot. This concentrates the activated plasmin where it is most needed. Streptokinase degrades not just fibrin, but also fibrinogen, depleting the blood's normal clot-forming ability. Further unlike streptokinase, u-PA and t-PA are direct activators of plasminogen, can be highly purified, and are not bacterial in origin and therefore do not produce a reaction.

One therapeutic disadvantage of t-PA and u-PA is that they are rapidly inactivated by plasma PAIs, particularly PAI-1, following administration of the therapeutics. Recombinant PA derivatives with resistance to inactivation could theoretically yield higher plasma PA levels over a longer time, with higher thrombolytic potency.

It is therefore an object of the present invention to provide a biologically active prourokinase/urokinase that is more resistant to inhibition by plasminogen activator inhibitors.

It is a further object of the present invention to provide vectors containing sequences encoding the resistant prourokinase/urokinase which can be used to incorporate the genes into a transgenic animal for tissue specific expression which is not harmful to the host animal, especially expression in high levels in the milk of a transgenic animal.

It is another object of the present invention to provide vectors encoding short sequences of prourokinase/urokinase, and methods of use thereof, for ease in altering binding sites for plasminogen activator inhibitors.

SUMMARY OF THE INVENTION

Mutants of human urokinase have been produced which have an altered amino acid sequence in the domain responsible for binding of plasminogen activator inhibitor(s). One example of an inhibitor resistant mutant is described in detail. Six amino acids (179–184), R H R G G S (SEQUENCE ID NO. 1), have been deleted from the mature urokinase. The modified urokinase was produced by chemically synthesizing a gene encoding inhibitor resistant pre-prourokinase according to computer-designed nucleotide sequences. The gene contains convenient restriction endonuclease cleavage sites, a signal for the initiation of translation, a sequence encoding the signal peptide of mouse whey acid protein and a complete coding sequence for mature inhibitor-resistant urokinase. The gene was synthesized in seven fragments and assembled together in a pUC derived vector, then inserted into a bovine papilloma virus based expression vector driven by the promoter from mouse metallothionein gene (Mt gene) and terminated by the SV40 polyadenylation site. The DNA was then transfected into a mouse fibroblast line, C127, to select for focus formation. The foci were isolated and analyzed for functional expression of inhibitor-resistant prourokinase/urokinase.

The clones with high levels of expression are used as the hosts for production of this protein. The DNA for the inhibitor-resistant prourokinase/urokinase, in combination with a tissue specific promoter, can also be introduced into fertilized embryos using standard techniques such as microinjection, the embryo implanted into a suitably prepared female of the same species, and the offspring analyzed for presence of the prourokinase/urokinase gene. The transgenic animals are bred and the lactating females tested for expression and secretion of the prourokinase/urokinase in the milk.

BRIEF DESCRIPTION OF THE DRAWINGS

FIG. 1 is a schematic of the cloning of a synthetic inhibitor resistant human urokinase: Panel A represents the complete plasmid construct used for transfection, with the positions of the mouse metallothionein promoter and SV40 polyadenylation signal indicated. Letters correspond to the restriction sites: B=BamHI (1; 13846); E=EcoRI (5608; 10286); S=SalI (7945); T=Taq I (Old Sal I - Xho I) (12286; 13603). Panel B represents an abbreviated restriction map of the synthetic urokinase gene. Letters correspond to the restriction map of the synthetic urokinase gene. Letters correspond to the restriction sites: Bg=Bgl II (345); Bs=Bst BI (143); C=Cla I methylated (926); E=EcoRI (1); H=Hind III (1335); N=Not I (542); P=Pst I (1173); S=Sal I (7;1324); X=Xho I (746).

FIG. 2 is the nucleotide and protein sequence (Sequence ID Nos. 2 and 3, respectively) of synthetic inhibitor-resistant human urokinase gene including sequence encoding the mouse whey acid protein signal. The upper box represents the 19 amino acid sequence of mouse WAP signal, while the lower box represent the six amino acids deleted from mut-uPA.

FIGS. 4A–4B are the kinetic analysis of mut-uPA graphing absorbance at 405 nm versus time for chromogenic substrate assay of syn-uPA partially inhibited with PAI-1 (ratio PAI-1:u-PA, fmol:fmol, 0.5:1). Curves represent 25 μM (squares), 50 μM (+'s), 75 μM (diamonds), 125 μM (triangles), 250 μM (X's), and 1000 μM (inverted triangles) of Spectrozyme substrate. FIG. 4B represents a Lineweaver-Burk plot (Min/OD 405 nm versus substrate concentration 1/mM) of data obtained from FIG. 4A for std-uPA (squares), syn-uPA (+'s), mut-uPA (diamonds), and the respective three samples in the presence of 0.5:1 fmol:fmol ratio of PAI-1:u-PA (triangles, x's, and inverted triangles, respectively). Km values were approximated by extrapolating the curves to the negative X-axis.

DETAILED DESCRIPTION OF THE INVENTION

Figure 3A:
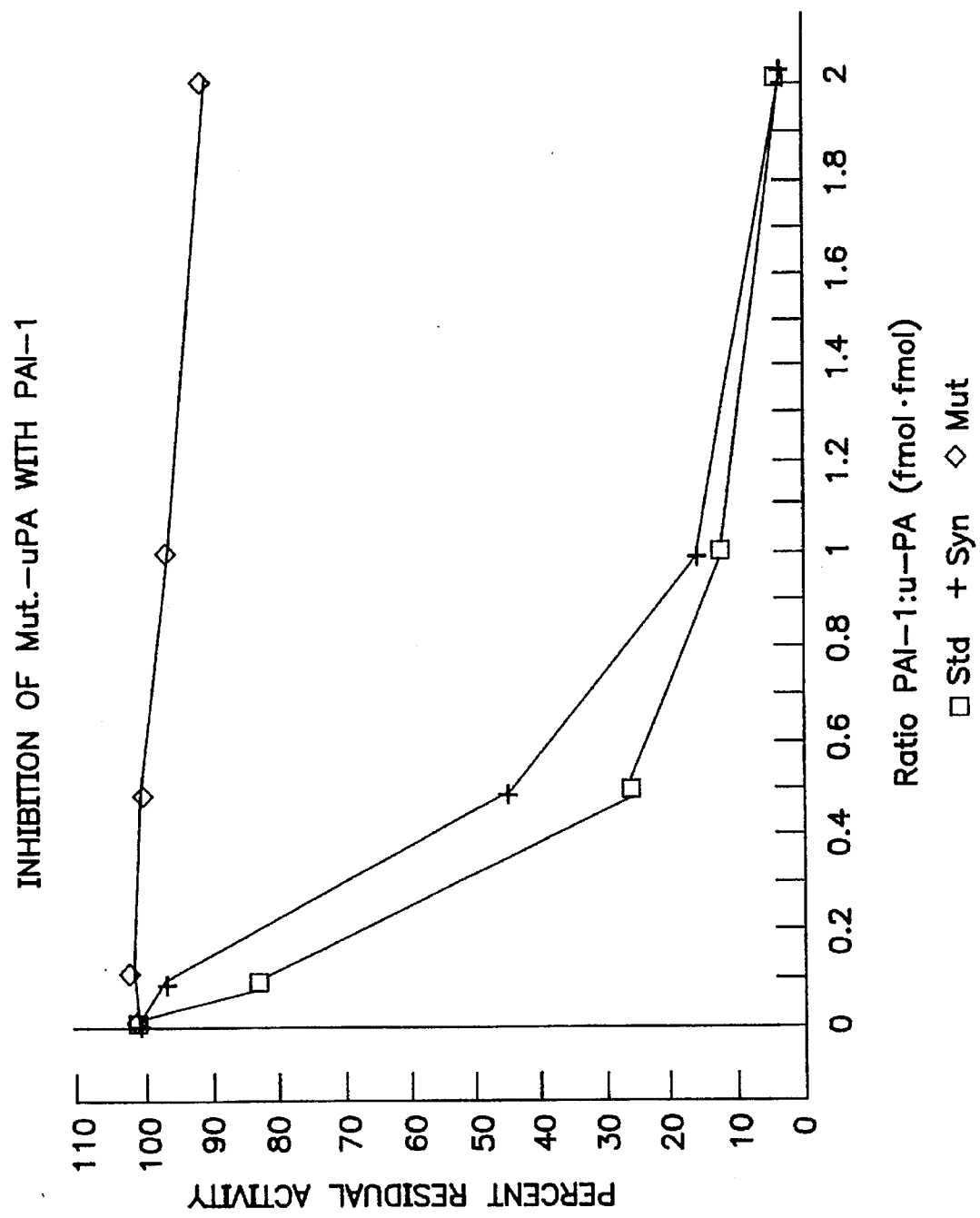
FIGS. 3A–3B are graphs of percent residual activity versus ratio of PAI-1:u-PA (fmol:fmol) (FIG. 3A) or PAI-2:u-PA (fmol:fmol) (FIG. 3B): std-uPA (squares), syn-uPA (+), and mut-uPA (diamonds) with PAI-1. Plasmin-activated media samples were preincubated 37° C. for 10 min with various amounts of inhibitor (ratio PAI-1:u-PA, fmol:fmol, 0:1, 0.1:1, 0.5:1, 1:1, 2:1) prior to determination of percent residual activity by a chromogen-cleavage assay.

Although it has been long recognized that there is a need for urokinases having a decreased susceptibility to inhibition by plasminogen activation inhibitors, the lack of a crystallographic structure for any PAI or serpin-protease complex has made it difficult to design an inhibitor resistant urokinase plasminogen activator (u-PA). An indirect approach has been used to design an urokinase which subsequently proved to be more inhibitor resistant than an unmodified urokinase (as shown in FIG. 1).

As noted above, tissue plasminogen activator (t-PA) has a similar function to urokinase but has a different amino acid sequence and structure, as well as mechanism of action. t-PA has a high affinity for fibrin clots and the enzymatic activity is activated by fibrin binding. In contrast, urokinase has no affinity for fibrin clots. More importantly, t-PA is an active enzyme in both one-chain or tw-chain forms, whereas prourokinase (one-chain form) is an inactive zymogen which has to be activated by plasmin to become active urokinase. In terms of inhibition by various PAIs, t-PA and u-PA show different patterns of inhibition by various PAIs, suggesting that the sites for PAI binding and interaction could be different. Madison et al., *Nature* 339: 721–724 (1989) showed that deletion of t-PA residues 296–302, conversion of Arg304 to Set304, or conversion of Arg304 to Glu304, resulted in a PAI-1-resistant PA with no alterations in catalysis or affinity for plasminogen. In a follow-up study (Madison et al., 1990), they showed similar results by replacing Lys296, Arg298, and Arg299 with negatively charged Glu residues, indicating that ionic bonds between positively charged residues in a surface loop near the active site and negatively charged residues on PAI-1 are responsible for the interaction.

A contact point for urokinase at position 304 was on the theory that urokinase may interact via ionic bonds between positively charged residues in a surface loop near the active site, in a similar fashion to t-PA. Urokinase has an additional 6 amino acids inserted adjacent to the predicted contact at position 304. Three of these 6 amino acids are positively charged (179, 180, 181) and represent excellent candidates for interaction with PAI-1. In addition, Arg178 is also positively charged. Considering ionic interactions only (not van der Waals), no other amino acids in u-PA region 185–194 are to interact with PAI-1.

Based on these kinds, it was decided to delete six amino acids (Arg179 to Ser184) from urokinase. The data indicate that the mutant u-PA has enzymatic properties similar to authentic u-PA, but shows significant resistance to inhibition by PAI-1 and PAI-2.

As described below, the sequence encoding the inhibitor binding regions can be selectively modified by synthesizing sequences having substituted amino acid. Modifications can also be made by site-directed mutagenesis. The synthetic sequences were inserted into seven vectors to facilitate construction of a modified sequence encoding the inhibitor-resistant urokinase. Other urokinases can be similarly produced.

The modified urokinase is expressed using standard techniques from bacterial or eucaryotic cell cultures, or in the milk of a transgenic animals. As described below, the gene is synthesized in several fragments and assembled in a pUC derived vector. It is subsequently inserted into an expression vector driven by the promoter from mouse whey acid protein gene, or other suitable tissue specific promoter, and terminated by the SV40 polyadenylation site. The protein can then be expressed in cell culture or introduced into the genome of transgenic animals for tissue specific expression of the protein. The DNA construct is excised from plasmid sequences, purified and introduced into embryos of animals by DNA microinjection techniques. The injected embryos are then reimplanted into the oviducts of pseudopregnant foster mothers. The embryos are allowed to develop into transgenic animals. The female transgenic animals that carry the expressible preprourokinase transgene are mated, then milked after giving birth. The milk preparations from individual transgenic animals are analyzed for the presence of urokinase/prourokinase and producers are bred to form transgenic lines.

Inhibitor resistant urokinase/prourokinase producing animals can be produced by incorporation of any of the genes encoding biologically active, inhibitor resistant urokinase/prourokinase. As used herein, these genes are collectively referred to as urokinase/prourokinase genes, and include genes for the preprourokinase, prourokinase and/or urokinase. For tissue specific expression, a promoter sequence for any milk-specific protein can be used, for example, whey acid protein promoter, casein promoter, or beta lactoglobulin promoter. The production of foreign proteins in transgenic animals is an attractive alternative to bacterial or tissue culture fermentation as a means of producing large amounts of recombinant proteins. Successes have been reported, including the production of human alpha-1-anti-trypsin in mouse and sheep milk by Archibald, et al., *Proc. Natl. Acad. Sci. USA* 87, 5178–5182 (1990), and Clark, et al., *Bio/Technology* 7, 487–492 (1989), respectively, as well as the production of sheep beta-lactoglobulin and human t-PA in mouse milk by Simons, et al., *Nature* 328, 530–533 (1987) and Gordon, et al., *Biotechnology* 5, 1183–1187 (1987). Some proteins are present in milk at concentrations as high as 16 grams per liter, as reported by Clark, et al., *Trends in Biotechnology*, 5, 20–24 (1987).

The present invention will be further understood with reference to the following examples demonstrating design and construction of a sequence encoding an inhibitor-resistant prourokinase/urokinase, testing of biological activity and inhibition of the activity of the expressed protein.

The following abbreviations are used herein: bp, base pair(s); HRP, horseradish peroxidase; IU, international unit; mut-uPA, mutant synthetic u-PA; mut-uPA-DNA, mutant synthetic u-PA DNA; PA, plasminogen activator; PAI-1, epithelial-type plasminogen activator inhibitor; PAI-2, placental-type plasminogen activator inhibitor; PAGE, polyacrylamide gel electrophoresis; PBS, phosphate buffered saline, pH 7.4; scu-PA, single chain u-PA; SDS, sodium dodecyl sulfate; serpin, serine protease inhibitor; std-uPA, standard authentic u-PA; syn-uPA, synthetic u-PA; syn-uPA-DNA, synthetic u-PA DNA; tcu-PA, two chain u-PA; t-PA, tissue-type plasminogen activator; u-PA, urokinase-type plasminogen activator; WAP, whey acid protein.

The following materials and methods were used to construct the inhibitor resistant urokinase as described in FIG. 1. The teachings of the cited references for the techniques described herein are specifically incorporated.

MATERIALS AND METHODS

Oligomer Synthesis and Purification:

DNA sequences were optimized for mouse preferred codons and convenient restriction sites using the program GENEPRO (Riverside, Scientific, Seattle, Wash.). For ease of assembly, the DNA was divided into seven fragments. Four oligomers representing a modified pUC polylinker, and 78 oligomers representing the optimized human pre-prourokinase sequence were synthesized by Genetic Designs, Inc.; Houston, Tex. Sizes varied between 16–40 nucleotides.

Oligomer Kination and Assembly:

Oligomers were kinased and annealed essentially as described by Theriault,.et al., *Biotechniques* 6:470–473 (1988) with modifications. Approximately 1 µg of each purified oligomer for a specific DNA fragment were pooled, and the volume adjusted to 28.5 µl. To the mixture was added 3.5 µl of 10X Kination Buffer (0.5M Tris-HCl), 0.1M $MgCl_2$, 0.15M DTT), 1 µl of 20 mM ATP, and 2 µl (20 U) of polynucleotide kinass (Biolabs) to make 35 µl final reaction volume. The reaction was incubated for 1 h at 37° C. The oligomers were annealed by incubating the kination reaction as follows: 10 min 100° C., 30 min 65° C., 30 min 37° C., 60 min 16° C. Oligomer ligation was performed by adding 4 µl of 10X Ligation Buffer (0.25M Tris-HCl pH 7.8, 0.1M $MgCl_2$, 40 mM β-mercaptoethanol, 4 mM ATP) and 1 µl of T4 DNA Ligase (Biolabs). The reaction was continued at 160° C. for 1 h or overnight.

Vector ligations were performed using 0.1 µg vector DNA at 16° C. for 1 h. In some cases, the oligomer ligation reaction was directly mixed with appropriately cut vector DNA for further ligation. In other cases, the ligated u-PA DNA fragment was digested with the appropriate restriction nucleases to release doublets, triplets, etc., and the monomer fragment purified by polyacrylamide gel electrophoresis (PAGE) prior to ligation to vector DNA. Vector ligation reactions were purified by Gene-Clean (Bio-101™, BioLabs, Inc.) to remove non-ligated oligomers.

Bacterial Transformation and Screening:

The ligated DNAs were transformed into competent *E. coli* GM-2163 (dam⁻, dcm⁻, BioLabs) or DH-5α (Bethesda Research Laboratories).

DNA Sequencing:

The sequence of each newly cloned u-PA fragment was verified prior to final assembly into the full-length DNA. DNA was sequenced from mini-preps by the chain termination method of Sanger, et al., *Proc. Natl. Acad. Sci. USA* 74: 5463–5467 (1977) using Sequenase (U.S. Biochemical Corp.). Various purified u-PA oligomers were used as primers. On the average, mutation rates of about 1/500 were observed, necessitating the sequencing of several isolates for each DNA fragment. Once a set of seven correct DNA fragments were identified, final ligation resulted in the completed synthetic DNA.

Mutagenesis:

Nucleotides 618–635 were deleted from DNA fragment 4 by reassembling the fragment using modified oligomers. Fragment 4 present in syn-uPA-DNA was deleted, and replaced with the newly assembled mutant fragment to produce mut-uPA-DNA. Correct assembly was verified by DNA sequencing.

Construction of Expression Vector:

Expression vector pBMYxSV (12,529 bp) was constructed by recombining the 7945 N BamHI/SalI fragment of the BPV-1 genome, described by Reddy, et al., *DNA* 6:461–472 (1987) with the 4,584 N BamHI/SalI fragment of pMTxSVAR (pML-1; 4,843 bp) containing the β-lactamase gene, mouse metallothionein-I promoter, and SV40 polyadenylation signal. The synthetic u-PA DNA was excised from its pUC-derived vector by digestion with SalI to produce a 1317 bp fragment, which was inserted into the XhoI site of pBMTxSV to produce plasmid uPA-BMTxSV (13,846 pb).

Transfection:

Mouse C-127 mammary tumor cells (American Type Culture Collection) were cultured at 37° C. in Dulbecco's Modified Eagle Medium (DMEM) supplemented with 0.45% dextrose, 10% fetal calf serum, 0.292 mg/ml glutamine, 100 U/ml penicillin-streptomycin, with an atmosphere of 6.3% $CO_2$. Plasmid DNAs were purified as reported by Birnboim and Doly, *Nucl. Acids Res.* 7:1513–1523 (1979) and transfected into C-127 cells using the $CaPO_4$ method described by Reddy, et al., *DNA* 6:461–472 (1987). BPV-induced foci were isolated from the plate by cloning rings, and cultured in microtiter dishes. Conditioned media supernatants from microtiter dishes were assayed for PA-activity using a fibrin-clot assay.

Production of u-PA for Enzymatic Assay:

Clones showing the highest PA-activity in the clot assays were cultured to confluency. The medium was replaced with serum-free medium, and the flasks cultured for an additional 48 h. The conditioned medium was removed, brought to 50% glycerol and 0.02% $NAN_3$, and stored at −20° C.

Activation of u-PA by Plasmin:

Scu-PA was converted to tcu-PA by treatment of the cultured medium with plasmin, as described by Lijnen, et al., *Eur. J. Biochem.* 169:359–364 (1987) but with modifications. The conditioned medium was brought to 0.01% Tween™-20 and 0.1 U/ml plasmin (Boehringer), and incubated for 1 h at 37° C. Aprotinin (Sigma) was added to 40 KIU/ml to inhibit the plasmin. The incubation was continued at 37° C. for 10 min, then the samples stored at −20° C. Since the medium was previously brought to 50% glycerol, at no time did it freeze and thaw.

Fibrin-Clot Assay:

Qualitative determination of PA activity in cultured media was performed by a fibrin-clot assay as described by Jespersen and Astrup, *Haemostasis* 13:301–315 (1983), except the clot contained 1.25% low melting temperature agarose, 0.05 U/ml thrombin (Boshringer), 0.01 U/ml lys-plasminogen (Boehringer), 2 mg/ml fibrinogen (Sigma), and 1X PBS pH 7.4. The clot was polymerized into microtiter dish wells, then up to 50 µl of cultured medium was added to a cored hole in the center of each well. Plates were incubated at 37° C. for various times.

Chromogenic Substrate Assay:

Quantitative determination of PA activity in conditioned media was performed by a direct-substrate chromogen (Spectrozyme™) assay developed by American Diagnostica (Greenwich, Conn.), following manufacturer's recommendations, except incubations were for 2 h instead of 5 min. For inhibition studies, cultured medium was preincubated for 10 min at 37° C. with various amounts of PAI-1 or PAI-2 (American Diagnostica).

Immunoblot:

Immunoblots were performed essentially as described by Towbin, et al., *Proc. Natl. Acad. Sci. USA* 76: 4350–4354 (1979) for u-PA as modified by Wagner and Binder, *J. Biol. Chem.* 261: 14,474–481 (1986). Apparent molecular weights (MW) were estimated by comparison with the relative migration of a prestained standard (BRL). Incubations with the primary antibody (goat anti-human u-PA IgG, American Diagnostica #398) were at 5 µg/ml in PBS-GT (1X PBS pH 7.4, 3% w/v gelatin, 0.2% v/v Tween™-20) for 12 to 24 h. Incubations with the secondary antibody (rabbit anti-goat IgG conjugated to alkaline phosphatase; Sigma A-2168) were at 1:1000 dilutions on the conjugate solution in PBS-GT for 4 to 8 h. The NBT-BCIP (BRL) color reaction was performed as recommended by the manufacturer. Membranes were stored in TE buffer, in the dark at 4° C.

Gel Overlay Assay:

This assay was performed essentially as described by Nagamine, et al., *Cell* 32:1181–1190 (1983) and Meade, et al., *Biotechnology* 8:443–446 (1990) except the overlay composition was 1.25% low melting temperature agarose, 2% casein (Sigma), 0.01 U/ml lys-plasminogen (Boehringer), and 1X PBS pH 7.4. Briefly, electrophoresis was as described above using non-reducing conditions. The acrylamide gel was washed in 2.5% Triton X-100 for 1 h at 25° C., and rinsed in dH$_2$O to remove the SDS. The acrylamide gel was placed on top of the pre-solidified agarose-casein-plasminogen solution. The gel "sandwich" was then sealed in a bag to prevent dehydration, and incubated overnight at 37° C. The acrylamide gel was separated from the agar, and the agar stained with amido black (Sigma) to reveal the zones of PA activity as cleared regions of casein hydrolysis.

ELISAs:

The mass of u-PA antigen in conditioned medium was quantified by ELISA using buffers and incubations recommended in the specification sheet for IMUBIND (American Diagnostica #844) and a combination of antibodies determined to react with mut-uPA by immunoblot analysis. Coating was with 10 µg/ml anti-u-PA mAb (American Diagnostica #390). Primary antibody was 10 µg/ml polyclonal anti-uPA (American Diagnostica #398). Secondary antibody was rabbit anti-goat IgG conjugated to HRP (Sigma #A-3540, 1:5000 dilution in Blocking Buffer).

Chemical Synthesis of DNA Encoding Urokinase

DNA synthesis and recombinant DNA techniques were used to produce a synthetic u-PA gene (syn-uPA-DNA), as shown in FIG. 1. u-PA DNA sequences were optimized for mouse preferred codons to facilitate subsequent expression in a mouse cell line and convenient restriction sites to facilitate subsequent mutagenesis. The 78 oligomers representing syn-uPA-DNA were 1640 nucleotides long. For ease of assembly, the gene was divided into seven fragments, as diagramed in FIG. 1B. The length of the synthetic u-PA gene as originally assembled in a modified pUC vector was 1335 N, but was 1317 N as a SalI fragment, as shown in FIG. 1A. The SalI u-PA fragment was inserted into the XhoI site of expression vector pBMTxSV. The expression vector contains the 7945 N BamHI/SalI BPV-1 genome and the 4,584 N BamHI/SalI pML-1 vector containing the β-lactamase gene, mouse metallothionein-I promoter, and SV40 polyadenylation signal, as shown in FIG. 1A.

Once assembled and cloned, the sequence of syn-uPA-DNA was verified by dideoxynucleotide sequence analysis. The complete sequence is shown in FIG. 2, and is available in the EMBL database (accession number X54317). The sequence contains one ATG signal for translational initiation (27–29), a 19 amino acid signal sequence for mouse whey acid protein (WAP) (27–83,upper box in FIG. 2), an optimized complete coding sequence for human pre-prourokinase (a and b-chains; enzyme commission number EC 3.4.21.31, reported by Verde, et al., *Proc. Natl. Acad. Sci. USA* 81:4727–4731 (1984), and one TGA signal for translational termination (position 1317–1319). The 430 amino acid sequence deduced from the synthetic DNA is identical to the urokinase portion of Verde, et al., (1984), however Met213 in the synthetic protein (Met194 excluding the signal) corresponds to Ile214 (Ile194 excluding the signal) in Nagai, et al. *Gene* 36: 183–188 (1985).

Once the assembly of syn-uPA-DNA was complete, mut-uPA-DNA was assembled. Nucleotides 618–635 (lower box in FIG. 2) were deleted from gene fragment 4 by reassembling the fragment using modified oligomers. Fragment 4 in syn-uPA-DNA was deleted, and replaced with the newly assembled mutant fragment to produce mut-uPA-DNA. Correct assembly was verified by DNA sequencing.

Expression of Urokinase in Mouse Cells

Once both synthetic genes were assembled and cloned, the DNAs were used to transfect a mouse cell line. The BPV-1 genome in the DNA served as a visual indicator of transfection. BPV-induced foci were isolated from the plate by trypsinization, and cultured in microtiter dishes. Conditioned media supernatants from microtiter dishes were assayed for plasminogen activator (PA) activity using the fibrin-clot assay. No PA activity was observed in the medium until foci formation had occurred. One clone showing the highest syn-uPA activity, and one showing the highest mut-uPA activity, were cultured in T-150 flasks to confluency. The medium was replaced with serum-free medium, and the flasks cultured for an additional 48 h. The cultured medium was then removed and assayed.

Syn-uPA and mut-uPA were analyzed by immunoblot under reducing and non-reducing conditions. Results are compared with 20 µg/band of prestained high molecular weight protein markers (BRL). 25 ng of syn-uPA were run against the controls, non-transfected control medium. The urokinase in each case has a molecular weight of approximately 54,000 daltons. For either treatment, both types of u-PA migrate as single bands in the 54,000 MW range. A single 54,000 dalton band present under reducing conditions indicates that the u-PA is secreted predominately in proenzyme (non-activated, single-chain) form. In some studies, a 33,000 band, representing activated two-chain form, was present in trace amounts. This slight activation may result from trace amounts of plasmin present in the serum-containing medium prior to its replacement with serum-free medium. A single 54,000 dalton band present under non-reducing conditions, rather than a 33,000 dalton band representing degraded enzyme, indicates that the u-PA is secreted in high-molecular-weight form (the primary antibody used in the blot can detect degraded low-molecular-weight forms of urokinase. No u-PA antigen was detected in non-transfected control medium, indicating no u-PA contamination from the serum-free medium. These results indicate that synthetic u-PA is secreted in native high-molecular-weight form in the culture medium.

Plasmin Activation of Synthetic Urokinase

Since most of the u-PA was secreted as pro-uPA, it was necessary to activate the urokinase to tcu-PA prior to further analysis. Four different activators were tested: kallikrein, plasmin, kallikrein with chondroitin sulfate C, and plasmin with chondroitin sulfate C. Immunoblot analysis indicated that plasmin treatment was most efficient. Kallikrein-treated samples showed no increase in activation. Addition of chondroitin sulfate C to kallikrein or plasmin-treated samples produced results no different from those with kallikrein or plasmin in the absence of chondroitin sulfate C. These results indicate that plasmin can be used to activate scu-PA directly in culture medium without prior purification of the u-PA, rather than after partial purification, as previously reported. Based on these results, plasmin was used for activation for all subsequent experiments.

Immunoblot analysis under reducing conditions was used to monitor the decrease of the 54,000 MW band, and the increase of the 33,000 MW band, during the activation of scu-PA by plasmin. The chromogen cleavage assay was used to monitor the increase in PA activity associated with activation. For both syn-uPA and mut-uPA, activation was nearly complete after 30 min, and complete after 1 h. The increase in PA activity observed after plasmin treatment is not due to the added plasmin since all samples were treated with the plasmin-inhibitor aprotinin prior to assay, and these values were used as background. Control samples using non-transfected medium showed no activity. Control samples using non-transfected medium treated with plasmin and aprotinin showed no activity. The results indicate that one hour is optimum for activation of the samples with plasmin. These conditions were used for all subsequent studies.

In order to verify that the PA activity observed in the activated medium associates with a protein the size of urokinase, a casein-plasminogen-agar overlay assay was performed. In this assay, samples were electrophoresed under non-denaturing conditions. Half the gel was used for immunoblot analysis, while the other half was washed to remove all SDS, then overlaid with a gel containing casein and plasminogen. Regions of the gel that contained u-PA activated the plasminogen to plasmin, which hydrolyzed the casein. The regions of casein hydrolysis were then revealed by staining with amido black. Non-plasmin-activated non-reduced syn-uPA migrated as a single 54,000 MW band on immunoblot, but showed relatively little PA activity. The same sample plasmin-activated also migrated at 54,000 MW on immunoblot but showed considerable PA activity. Mut-uPA showed identical results. The plasmin added to the samples for activation is not responsible for the observed zones of PA activity since "activated" control medium from non-transfected cells showed negative results. These results demonstrate that the PA activity observed in the culture media associates with a protein the size of urokinase.

Mut-uPA is as Active as syn-upA

Once optimal activation conditions were determined, the activity and mass relative to standard u-PA (std-uPA) were determined so that specific activities could be compared. The mass of urokinase antigen present in the culture media was determined by ELISA. The commercially available ELISA Imubind Kit (#844, American Diagnostics) proved unsuitable for analyzing mut-uPA. Western analysis revealed that the detecting antibody in this kit (Reagent C) reacted with syn-uPA, but not mut-uPA. Thus, Reagent C probably recognizes, in part, the 6 amino acid epitope removed in the mutant. Western analysis of culture media using several commercially available antibodies indicated that the following reacted with both syn-uPA and mut-uPA: mAbs #377, #390, #394, #3921 (anti-A-chain), and polyclonal #398 (American Diagnostics), however only mAb #390 proved suitable for coating.

The concentration of syn-uPA was determined to be 2150 ng/ml (2.15 mg/l), and that of mut-uPA 333 ng/ml (0.3 mg/l). Although the concentration of mut-uPA was found to be less than that of syn-uPA in these two particular clones, due to the low numbers of clones screened for PA activity no conclusions regarding a potential decreased secretion rate for mut-uPA can be drawn. The mass of u-PA antigen for both samples slowly decreased over several months of storage, even when stored in 50% glycerol to prevent freeze-thawing. Thus, the concentration values given above are for relatively new cultures. Chromogen-cleavage assay of PA activity in each activated sample relative to that of std-uPA gave the following results: syn-uPA 1032 IU/ml, mut-uPA 160 IU/ml. Dividing the activities by the masses gave nearly identical specific activities for both enzymes ($4.8 \times 10^5$ IU/mg u-PA). The specific activity values were slightly higher than that of the standard ($3.6 \times 10^5$ IU/mg u-PA, Calbiochem Inc. #672123).

Mutant Urokinase is Resistant to PAI-1 and PAI-2

Figure 3B:
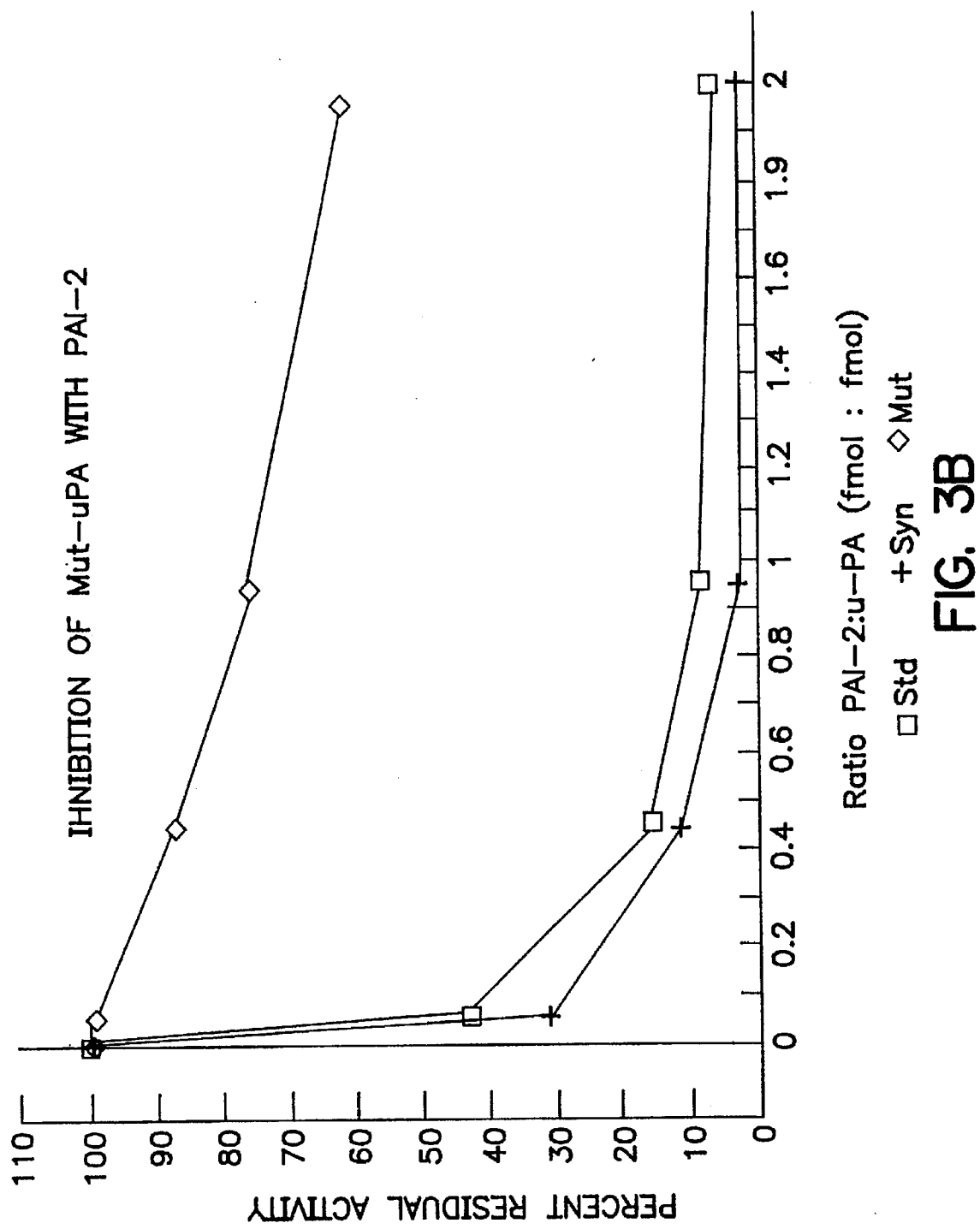

In order to determine whether mut-uPA was resistant to inhibition by PAI-1 or PAI-2, activated u-PA samples were mixed with increasing amounts of inhibitor, and residual PA activity quantified by chromogenic substrate assay (FIGS. 3A and 3B).

FIG. 3A demonstrates that under conditions where only 10% of syn-uPA or authentic u-PA (std-uPA) activity remains (1:1 molar ratio PAI-1:u-PA), 95% of mut-uPA activity remains. In a separate study with PAI-1, at a molar ratio of 10:1 PAI:mut-uPA, 30% of mut-uPA activity remained. FIG. 3B shows an identical study conducted with PAI-2, and the results are similar to those with PAI-1 except mut-uPA shows 80% residual activity at a 1:1 ratio. These results indicate that mut-uPA is resistant to inhibition by either PAI-1 or PAI-2, and indicate that the six amino acids deleted from the mutant are responsible, in part, for binding the inhibitor.

In order to-determine whether the deletion of the six amino acids altered the kinetic properties of the enzyme, a kinetic analysis was performed. In this assay, OD versus time for the chromogen-cleavage assay was monitored at various substrate (Spectrozyme™) concentrations. The linear portions of each curve (FIG. 4A for syn-uPA as an example) were used to construct a Lineweaver-Burk plot (FIG. 4B). Without PAI-1 present, identical Km values (0.20 mM) were observed for syn-uPA, mut-uPA, and std-uPA. In the presence of PAI-1 at a 0.5:1 molar ratio, the Km values of syn-uPA and std-uPA increased to 0.67 mM, while mut-uPA increased to only 0.25 mM. These Km values are in the range expected for a Spectrozyme™ reaction conducted at 25° C. (Spectrozyme™ Specification Sheet, American Diagnostica). The data indicate that in the presence of inhibitor, mut-uPA has kinetic properties more closely related to uninhibited syn=uPA and std=uPA. An unaltered Km in the presence of inhibitor for mut-uPA implies that the 6 amino acid deletion has no effect on the affinity of the enzyme for its substrate. The deletion of amino acids 179–184 from mut-uPA renders the enzyme resistant to inhibition by PAI-1 and PAI-2, while not affecting enzymatic properties.

Mut-uPA was also Shown to be resistant to PAI-2, although there is little sequence homology between PAI-1 and PAI-2.

The use of urokinase variants resistant to inhibition by PAI-1 may offer a promising approach for maintaining urokinase in an active form in the circulation of patients treated for myocardial infarction.

Although the resistance of mut-uPA to PAI-1 inhibition is quite complete, a more detailed mutational analysis can be used to define more precisely other potential PAI-1 binding domains. One candidate for deletion is Arg178 since it is the only positively charged amino acid remaining in the 159–188 loop of mut-uPA.

The mutagenesis approach could be used to provide u-PA with useful properties in addition to PAI resistance. Recent studies with t-PA have shown that variants with decreased in vivo clearance can result in more potent thrombolytic agents. For uPA, the E domain is a prime candidate for deletional analysis. Deglycosylated variants of t-PA exhibit increased fibrinolytic activity. Urokinase also has glycosylation sites that can be modified or deleted, or the protein deglycosylated by chemical or enzymatic treatment, or by expression in a system such as bacteria where the resulting protein is not glycosylated. Substitutions in the Leu144 to Lys158 region have been used to enhance the fibrin affinity of urokinase, as reported by Homandberg and Wai, *Thrombin Res.* 58:403–412 (1990). Hybrid enzymes composed of the A-chain of plasmin, and the B-chain of urokinase have been shown to have enhanced fibrin-binding capacity by Fears, et al., *Biochem. J.* 266: 693–696 (1990).

Introduction of the construct into mammalian cells and embryos for expression.

The construct is introduced into the genome of mammals such as mice, rats, sheep, cattle, and pigs for expression and secretion into the milk using standard techniques, for example, as follows.

Animals and embryos:

Mice are obtained from Charles River Laboratories, Boston, Mass. and Jackson Laboratories, Ma. Reagents such as bovine serum albumin, gelatin, and pronase are obtained from Sigma Chemical Co., St. Louis, Mo. Hormones for superovulation, PMS and hCG, are obtained from Organon, Inc., N.J. Hyaluronidase is purchased from Sigma. Restriction enzymes are obtained from Biolabs, Beverly, Mass. The micromanipulator made by Nara Shige, USA, Inc., Rainin Instruments Co., Woburn, Mass., is used to microinject DNA into the pronuclei. DMEM, fetal bovine serum, and DPBS are supplied by GIBCO Laboratories, Gaithersville, Md.

Procedures for embryo manipulation and microinjection are described in "Manipulating the Mouse Embryo" by B. Hogan, F. Costantini and E. Lacy (Cold Spring Harbor Laboratory, 1986), the teachings of which are incorporated herein.

Mouse zygotes are collected from six week old females that have been superovulated with pregnant mares serum (PMS) followed 48 hours later with human chorionic gonadotropin. Primed females are placed with males and checked for vaginal plugs on the following morning. Pseudopregnant females are selected for estrus, placed with proven sterile vasectomized males and used as recipients. Zygotes are collected and cumulus cells removed by treatment with hyaluronidase (1 mg/ml).

Pronuclear embryos are recovered from female mice, such as B6D2, mated to males, such as CDI. Females are treated with pregnant mare serum, PMS, (5 IU) to induce follicular growth and human chorionic gonadotropin, hCG (51 U) to induce ovulation. Embryos are recovered in a Dulbecco's modified phosphate buffered saline (DPBS) and maintained in Dulbecco's modified essential medium (DMEM) supplemented with 10% fetal bovine serum.

Microinjection:

Microinjections are performed using Narishige micromanipulators attached to a Nikon disaphot microscope. Embryos are held in 100 microliter drops of DPBS under oil while being microinjected. DNA solution is microinjected into the largest visible male pronucleus. Successful injection is monitored by swelling of the pronucleus.

Embryo transfer:

Immediately after injection embryos are transferred to recipient females, mature mice, such as CDI mice, mated to vasectomized male mice, such as CD mice. Recipient females are anesthetized using 2,2,2 tribromoethanol. Paralumbar incisions are made to expose the oviducts and the embryos are transferred into the ampullary region of the oviducts. The body wall is sutured and the skin closed with wound clips. Recipients are appropriately ear notched for identification and maintained until parturition.

Sampling for DNA integration:

At three weeks of age about 2–3 cm long tail samples are excised for DNA analysis. The tail samples are digested by incubating overnight at 55° C. in an incubator in the presence of 0.7 ml 50 mM Tris, pH 8.0, 100 mM EDTA, 0.5% SDS and 350 µg of proteinase K. The digested material is extracted once with an equal volume of phenol and once with an equal volume of phenol:chloroform (1:1 mixture). The supernatants are mixed with 70 µl 3M sodium acetate (pH 6.0) and the DNAs are precipitated by adding equal volume of 100% ethanol. The DNAs are spun down in a microfuge, washed once with 70% ethanol, dried and dissolved in 100 µL TE buffer (10 mM Tris, pH 8.0 and 1 mM EDTA). 10 to 20 µl of DNAs are cut with BamHI and BglII or EcoRI, electrophoresed on 1% agarose gels, blotted onto nitrocellulose paper and hybridized with $^{32}$P-labeled mut-uPA DNA sequences. Transgenic animals are identified by autoradiography.

Propagation of transgenic mice:

At five weeks of age transgenic female mice are mated to CDI males. At six to seven weeks of age transgenic males are mated to two CDI females. The F1 litters are analyzed for transgenes.

Identification of mut-uPA in the milk and sera of transgenic mice:

After successful pregnancy followed by birth of litters, transgenic females are milked during the second week of lactation. Milk samples (50–200 µl) are collected from anesthetized mice injected with 0.05 units of oxytocin, to stimulate milk letdown. The milk is collected in a glass capillary by mammary palpation and frozen in microfuge tubes for assay.

Blood samples (100–200 µl) are collected by cutting the caudal vein with a scalpel. The samples are allowed to coagulate and spun down and the supernatants are collected in microfuge tubes and frozen.

Modifications and variations of the vectors and methods for use thereof in the production of inhibitor-resistant prourokinase/urokinase will be obvious to those skilled in the art from the foregoing detailed description. Such modifications and variations are intended to come within the scope of the appended claims.

---

We claim:

1. A modified urokinase that cleaves plasminogen, wherein the modified urokinase is encoded by a nucleotide molecule wherein the codons encoding Arg His Arg Gly Gly Ser (SEQ ID NO: 1) at positions 179–184 have been deleted, and wherein the urokinase has a lower binding affinity for plasminogen activator inhibitor-1 than does unmodified urokinase including the amino acid sequence Arg His Arg Gly Gly Ser (SEQ ID NO: 1).

2. The urokinase of claim 1 further comprising the signal peptide of whey acid protein.

3. The urokinase of claim 1 having a decreased affinity for plasminogen inhibitor-2.

4. The urokinase of claim 1 expressed in the milk of transgenic animals.

5. The urokinase of claim 1 having a decreased amount of glycosylation over unmodified urokinase.

6. The urokinase of claim 5 wherein the protein has fewer glycosylation sites than the unmodified urokinase.

7. The urokinase of claim 5 wherein the protein has enhanced fibrin affinity as compared to unmodified urokinase.

* * * * *